(12) United States Patent
Samuel et al.

(10) Patent No.: US 10,973,553 B2
(45) Date of Patent: Apr. 13, 2021

(54) MODULAR PEDICLE SCREW WITH MULTI-PART CAM LOCK STRUCTURE

(71) Applicant: Life Spine, Inc., Huntley, IL (US)

(72) Inventors: Forrest Samuel, Carlsbad, CA (US); Gregory Palagi, Geneva, IL (US)

(73) Assignee: LIFE SPINE, INC., Huntley, IL (US)

( * ) Notice: Subject to any disclaimer, the term of this patent is extended or adjusted under 35 U.S.C. 154(b) by 70 days.

(21) Appl. No.: 16/373,589

(22) Filed: Apr. 2, 2019

(65) Prior Publication Data

US 2019/0298418 A1 Oct. 3, 2019

Related U.S. Application Data

(60) Provisional application No. 62/651,390, filed on Apr. 2, 2018.

(51) Int. Cl.
*A61B 17/70* (2006.01)
*A61B 17/86* (2006.01)

(52) U.S. Cl.
CPC ...... *A61B 17/7032* (2013.01); *A61B 17/7037* (2013.01); *A61B 17/8605* (2013.01)

(58) Field of Classification Search
CPC ............ A61B 17/7032; A61B 17/7034; A61B 17/7035; A61B 17/7037
See application file for complete search history.

(56) References Cited

U.S. PATENT DOCUMENTS

| | | | |
|---|---|---|---|
| 2006/0155278 A1* | 7/2006 | Warnick | A61B 17/7037 606/278 |
| 2006/0200128 A1* | 9/2006 | Mueller | A61B 17/7037 606/308 |
| 2006/0233597 A1* | 10/2006 | Ensign | A61B 17/7049 403/177 |
| 2007/0093827 A1* | 4/2007 | Warnick | A61B 17/7032 606/86 A |
| 2007/0123862 A1* | 5/2007 | Warnick | A61B 17/7035 606/261 |
| 2010/0204735 A1* | 8/2010 | Gephart | A61B 17/7037 606/264 |
| 2012/0143266 A1 | 6/2012 | Jackson et al. | |

FOREIGN PATENT DOCUMENTS

EP 1 190 678 A2 3/2002
WO 2010/062736 A1 6/2010

* cited by examiner

*Primary Examiner* — Ellen C Hammond
(74) *Attorney, Agent, or Firm* — Foley & Lardner LLP (57) ABSTRACT

A modular pedicle screw assembly has a multi-part cam lock structure for fixing a threaded shank to a head subassembly. A modular pedicle screw assembly provides capture and release of a spherical end of a threaded shank by a head through rotation of closures radially disposed in an internal chamber of the head. Geometry of the closures cooperate with geometry of the internal chamber, providing a selective cam action between the closures and the internal chamber to increase and decrease size of an opening formed by the closures. Closure rotation produces an open state where the spherical end of the threaded shank can pass through the closures, releasing the spherical end of the threaded shank from the head, and a closed state where the spherical end of the threaded shank cannot pass through the closures thereby capturing the spherical end of the threaded shank in the head.

6 Claims, 12 Drawing Sheets

MODULAR PEDICLE SCREW WITH MULTI-PART CAM LOCK STRUCTURE

CROSS-REFERENCE TO RELATED APPLICATIONS

This U.S. non-provisional patent application claims the benefit of and/or priority under 35 U.S.C. § 119(e) to U.S. provisional patent application Ser. No. 62/651,390 filed Apr. 1, 2018 titled "Modular Pedicle Screw Allowing Repeated Assembly and Disassembly" the entire contents of which is specifically incorporated herein by reference.

FIELD OF THE INVENTION

The present invention relates to spine screw assemblies for spine fixation and, more particularly, to modular pedicle screw assemblies for spine rod applications.

BACKGROUND OF THE INVENTION

Many people contend with orthopedic issues as a result of age, disease and trauma, as well as congenital and acquired complications and conditions. While some of these conditions can be alleviated without surgery, other conditions require a surgical procedure. In some cases, the surgical procedure may include the insertion of an orthopedic implant. Orthopedic spine assemblies and constructs such as spine plates, bone screw assemblies for spine rods and other devices (spine components) have made a profound contribution to the correction of spinal deformities, accidents and other problems in the cervical as well as thoracic, lumbar and sacral spine. These and other spine devices are typically fixed to vertebrae using vertebral bone screws having specialized heads for holding a spine rod or other device. Vertebral bone screws are specially designed and manufactured bone screws that are placed into the bone of a vertebra and particularly, but not necessarily, in a pedicle of the vertebra. Vertebral bone screws placed in the pedicle of a vertebra offer superior strength and pull-out resistance as compared to other forms of fixation in spine surgery. The ability to achieve vertebral fixation has allowed surgeons to obtain more secure fixation of the spinal components involved, which permits more powerful correction of spine problems and reported better clinical outcomes.

In addition to other uses, pedicle screws provide a solid foundation for the attachment of spine rods used for the fixation of a two or more vertebrae. A spine rod is fixed relative to vertebrae either by a pedicle screw having a spine rod holder/head of a fixed angle, or a pedicle screw assembly having a multi or poly axial spine rod holder/head that allows adjustment of axial orientation of the pedicle screw relative to the spine rod holder/head. In all cases, however, spine rod pedicle screws and pedicle screw assemblies are fixed to a pedicle of a vertebra and hold a spine rod in a fixed position relative to the vertebra. Because of the design of spine rod pedicle screw assemblies, spine rods can thus be rigidly locked into a variety of positions along with other types of spine implant components. This allows a surgeon to tailor-make a spine construct on an individual basis.

Fixed angle spine rod pedicle screws either have a spine rod holder that is integral with a threaded shaft at a set angle, or a separate spine rod holder that is assembled onto a threaded shank. Fixed angle spine rod pedicle screws that are assembled provide greater flexibility for the surgeon during installation over fixed angle spine rod pedicle screws having an integral spine rod holder. It is thus preferable to use assembled fixed angle spine rod pedicle screws.

Assembled fixed angle spine rod pedicle screws have two components that need to be fixed together in a particular angular orientation, namely a pedicle (bone) screw and a spine rod holder. Because the assembly is used in the body, it is important that the locking structure be tough. It is thus necessary to provide a robust manner of joining and locking the two components together. One manner is to provide a separate locking mechanist in the spine rod holder. Another manner is to provide a locking structure as part of or integral with the spine rod holder. Yet another manner is a combination of both. However, the prior art assembled fixed angle spine rod pedicle screws are deficient in many respects.

Without being exhaustive, it is thus desirable to provide an assembled fixed angle pedicle screw having a mechanism for locking a pedicle screw to a spine rod holder at a fixed angle that is robust and easy to use. It is also desirable to provide a modular assembled fixed angle pedicle screw. It is also desirable to provide a modular assembled fixed angle pedicle screw with a robust and easy to use spine rod locking and unlocking structure. These and other needs are met by the present invention.

SUMMARY OF THE INVENTION

A modular pedicle screw assembly provides capture and release of a spherical end of a threaded shank by a head or spine rod holder through rotation of closures radially disposed in an internal chamber of the head. The geometry of the closures cooperate with geometry of the internal chamber to provide a selective cam action between the closures and the internal chamber to increase and decrease size of an opening formed by the closures.

Rotation of the closures produces an open state where the spherical end of the threaded shank can pass through the closures thereby releasing the spherical end of the threaded shank from the head, and a closed state where the spherical end of the threaded shank cannot pass through the closures thereby capturing the spherical end of the threaded shank in the head. Variation in the outer surface created by a change in width of the closure cooperates with variation in the circumferential configuration of the internal chamber to provide a cam structure between the closures and the internal chamber of the head that is selectively engaged through rotation of the closures relative to the internal chamber.

The modular pedicle screw assembly includes a shank, and a subassembly consisting of a head, a plurality of closures, and a ring. Features of the components of the subassembly allow for the subassembly to engage the proximal end of the shank, and upon a state change caused by rotation, secure it within the head, preventing it from disassembly.

The shank has at least one bone engagement surface such as, but not limited to threading, and two ends defining a central or longitudinal axis. One end defines a distal end of the shank that is preferably, but not necessarily, a tip, while the opposite end defines a proximal end of the implant has a feature compatible for assembly with the other subcomponents, such as, but not necessarily, a spherical surface.

The closure has three primary features. An outer feature is mostly defined by a largest first diameter, an innermost feature mostly defined by a smallest second diameter, and an interruption in geometry (variation) between the first and second diameters roughly defining a third in-between diameter. The interruption is a decrease in width that creates for camming or wedging surface that provides cam action between the closure and the internal chamber of the head.

The head holds together as a subassembly the ring, and at least one, but preferably, three closures within it. Two states exist with this subassembly. One state is an open state wherein the subassembly will allow the proximal end of the shank to pass into the subassembly. The second state is a closed state that prevents the shank from exiting the assembly.

The proximal end of the head is threaded in a way traditional to pedicle screws. The distal end of the head has an internal chamber where the closures reside. The internal chamber consists of at least one surface in a direction radial to a central axis of the head. The circumferential configuration consists of two surfaces repeated three times about the perimeter of the chamber, creating three radially narrowed portions. There is a first outer diameter that runs tangent to at least one outer most surface. There is a smallest through second diameter. There is lastly a third diameter between the first and second diameters via an interruption in geometry from the first diameter. In this embodiment, this interruption creates for a camming or wedging surface for the cam action between the closures and the internal chamber of the head.

Preferably, but not necessarily, three closures are used to capture the proximal end of the shank. As previously mentioned, two states are possible with the head subassembly; an open state where it will allow passage of the proximal end of the shank, and a closed state that will capture it and prevent it from disassembly from the head. This state change is created from positional rotation of the closures relative to the head about the central axis. To allow introduction of the shank, the through hole created by the second inner surface of the closure is such that it is close to or larger than that of the proximal end of the shank. This is possible when the outer most surfaces of the closures are in a first angular position, adjacent the outer most surfaces in the chamber of the head.

The through passage created in the open state can be larger than that of the proximal end of the shank. However, it can be slightly undersized so as to provide for a slight material interference upon introduction of the shank between the passing shank and the closures. This material interference can create for a tactile snap and/or auditory cue for partial assembly.

To capture the shank and prevent it from disassembly, the second closed state is utilized. This is achieved by rotating the closures about the central axis to a second position. This second position puts the outer most surfaces of the closures adjacent the inner most surfaces of the internal chamber in the head. This effectively reduces the through diameter to a value that will not permit the proximal end of the shank to pass back through. The transition from an open state to a closed state involves the geometric interruption on the inside of the chamber to cam or wedge against the geometric interruption on the outside of the closures, forcing a radial translation of the closures, narrowing the through passage of the subassembly.

The transition from the open state to the closed state is reversible. An equal rotation of the closures in the opposite direction back to the open state will create space for the closures to translate radially back into, effectively opening back up the through diameter of the subassembly so that the shank may be disengaged.

Once the open state has been regained, a force is introduced to pull the subassembly off of the shank. This will force the closures radially outward to restore the large through diameter.

Rotation of the closures is created with an applied torque to the ring. Misalignment of the rod slot of the ring with the rod slot of the head indicates an open state. When the closed state has been reached, the rod slot of the ring is parallel with that of the head.

Torque is translated through the ring into the closures via a loose mechanical attachment. This attachment is preferably, but not necessarily, an inter-digitation of axial flanges of the closures and ring, and slots for the flanges of the closures in the ring. The flanges of the ring apply a tangential force to those of the closure.

The present modular pedicle screw assembly is preferably, but not necessarily, a fixed angle modular pedicle screw assembly.

Further aspects of the present invention will become apparent from consideration of the drawings and the following description of the invention. A person skilled in the art will realize that other forms of the invention are possible and that the details of the invention can be modified in a number of respects without departing from the inventive concept. The following drawings and description are to be regarded as illustrative in nature and not restrictive.

BRIEF DESCRIPTION OF THE DRAWINGS

The above mentioned and other features, advantages and objects of this invention, and the manner of attaining them, will become apparent and the invention itself will be better understood by reference to the following description of an embodiment of the invention taken in conjunction with the accompanying drawings, wherein.

A description of the features, functions and/or configuration of the components depicted in the various figures will now be presented. It should be appreciated that not all of the features of the components of the figures are necessarily described. Some of these non-discussed features as well as discussed features are inherent from the figures. Other non-discussed features may be inherent in component geometry and/or configuration.

DETAILED DESCRIPTION OF THE INVENTION

Figure 1:
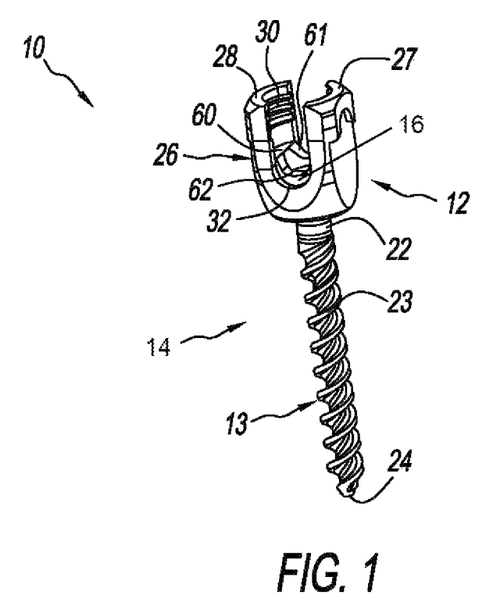
FIG. 1 is a perspective view of a modular pedicle screw with a multi-part cam lock structure fashioned in accordance with the present principles.

Referring to FIG. 1, there is depicted a pedicle screw assembly (or simply pedicle screw), generally designated 10, comprising a shank or screw 14 and a subassembly consisting of a head 12, one or more closures 18 (not seen in FIG. 1, see e.g., FIGS. 7, 8 and 13) and a ring 16, all fashioned in accordance with the present principles. The pedicle screw assembly 10 may be considered a modular pedicle screw assembly since it consists of the various components shown and described herein. FIGS. 2-36 depict views of the various components of the present pedicle screw assembly 10 as well as subassemblies and illustrative depictions thereof.

Figure 2:
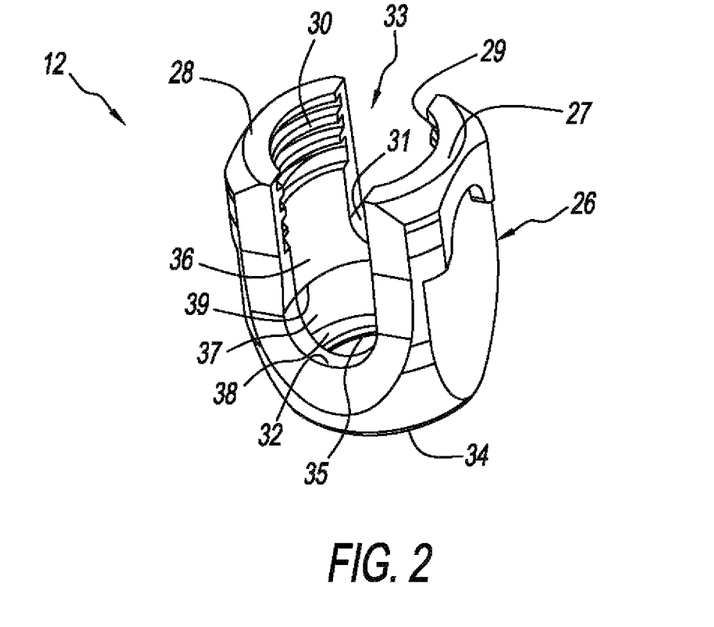
FIG. 2 is an enlarged perspective view of a head of the modular pedicle screw of FIG. 1.
Figure 15:
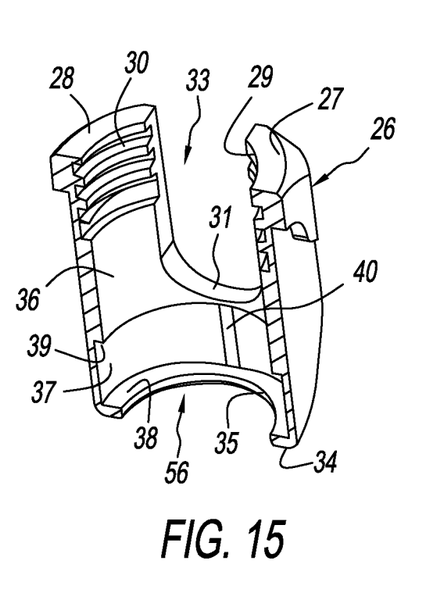
FIG. 15 is an enlarged sectional isometric view of the head of the modular pedicle screw of FIG. 1.
Figure 16:
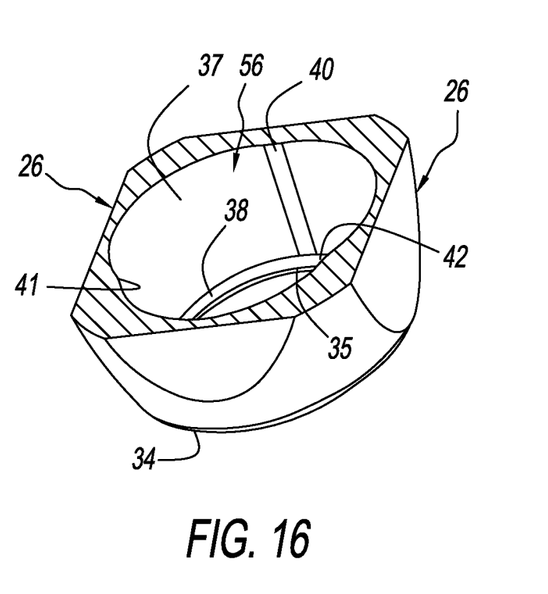
FIG. 16 is an enlarged sectional isometric view through a top surface of a chamber of a lower portion of the head of the modular pedicle screw of FIG. 1.

The head 12, as particularly shown in FIGS. 2 and 15, is characterized by a generally tulip-shaped body 26 configured to receive and retain a spine rod (not shown), and be received onto the shank 14 in the manner described herein. The body 26 has an axial bore 33 from a top of the body 26 to a bottom 34 of the body 26 that defines a first curved wall or side 27 and a second curved wall or side 28, the nomenclature first and second being arbitrary here and throughout unless otherwise indicated. The bore 33 has a circumferential opening 35 at the bottom 34 of the body 26. Threads or threading 29 is provided on an inside curved surface of the first curved wall 27 that extend from proximate a top of the inside surface of the first curved wall 27 an axial distance distally therefrom. Threads or threading 30 is also provided on an inside curved surface of the second curved wall 30 that extend from proximate a top of the inside surface of the second curved wall 28 an axial distance therefrom. The axial distances of the threading 29 and 30 being preferably, but not necessarily, generally the same. The threading 29, 30 is configured to receive a threaded set screw (not shown) such as is known in the art for securing a spine rod (not shown) in the body 26, particularly within the bore 33. As such, the body 26 has a first cutout 31 between a first lateral side of the first curved wall 27 and a first lateral side of the second curved wall 28 that is opposite the first lateral side of the first curved wall 27, and a second cutout 32 between a second lateral side of the first curved wall 27 and a second lateral side of the second curved wall 28 that is opposite the second lateral side of the first curved wall 27. The cutouts 31, 32 are opposite one another and are configured to hold a cylindrical spine rod (not shown) such as is known in the art.

Figure 17:
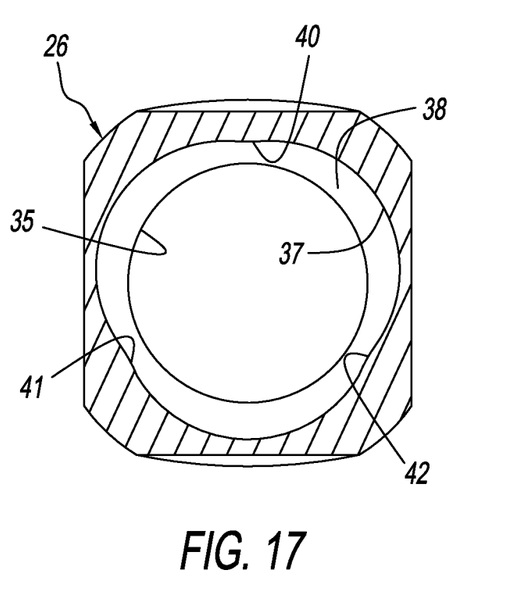
FIG. 17 is a top plan (axial) sectional view of the chamber of the lower portion of the head of the modular pedicle screw of FIG. 1.
Figure 18:
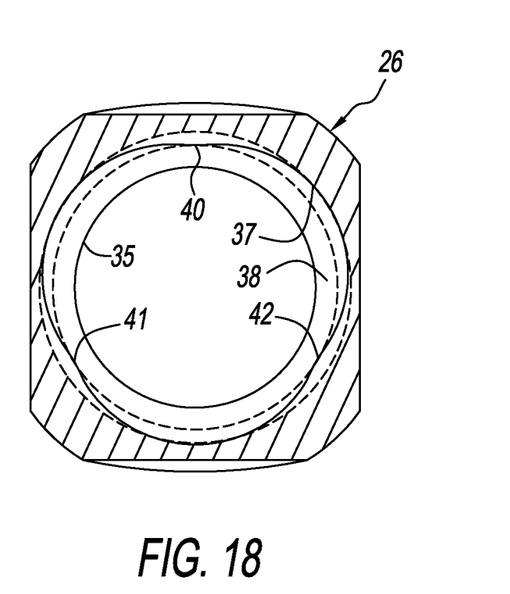
FIG. 18 is the top plan (axial) sectional view of FIG. 17 with two superimposed circles drawn thereon to highlight two characteristics of the chamber of the lower portion of the head of the modular pedicle screw of FIG. 1.

As discerned in FIGS. 15-18, and in accordance with the principles of the present invention, the head 12 has an internal chamber 56 disposed proximate the bottom 34 of the body 26. The chamber 56 is generally a circumferential cutout or notch in the interior surface of the body 26 that extends axially from a circumferential overhang 39 to a circumferential ledge 38. The circumferential overhand 39 provides/defines an upper seat or limit, while the circumferential ledge 38 provides/defines a lower seat or limit for holding a closure 18 therein. A circumferential surface 37 of the internal chamber 56 is configured to allow one or more closures 18 that is/are disposed in the internal chamber 56 to move radially inward and outward, depending on their rotational position within the internal chamber 56 by providing a cam or camming effect at certain circumferential positions. FIG. 17 shows that the circumferential surface 37 of the internal chamber 56 is not a circle but includes preferably, but not necessarily, three (3) surface interruptions, inflections, or variations 40, 41, 42 that are preferably, but not necessarily evenly spaced about the circumference. Each surface interruption 40, 41, 42 is a curved radially inward projecting bump or bulge. As illustrated in FIG. 18, two (2) dashed circles have been superimposed over FIG. 17 to highlight the characteristics of the interior chamber such as the outer wall surface variations. The chamber has a first outermost diameter (illustrated by a radially outermost dashed circle) that runs tangent to at least one outermost circumferential surface 37 of the interior chamber. There is a smallest diameter defined by the bottom hole 35 of the ledge 38. Lastly, there is a third (3) diameter (illustrated by a radially innermost dashed circle) that is between the first and second diameters via the interruptions 40, 41, 42 in geometry from the first diameter. The interruptions 40, 41, 42 creates for a camming or wedging surface.

Figure 11:
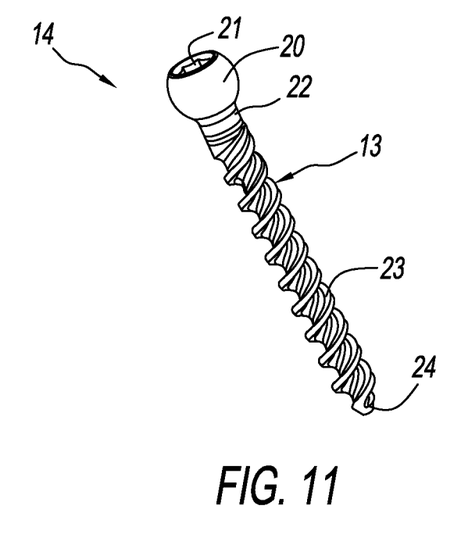
FIG. 11 is a perspective view of a bone screw of the modular pedicle screw of FIG. 1.

The shank 14 is characterized by an elongate body 13 defining a distal end 24 that is preferably, but not necessarily, formed as a tip or point, and a proximal end 20 that is preferably, but not necessarily, formed as a spherical surface. The elongate body 13 also defines an externally threaded shaft 23, the threading configured to pedicle/vertebral bone attachment. The proximal spherical surface 20 extends axially from the threaded shaft 23 and includes a socket 21 that is configured to receive a shank installation tool (not shown). In one form, the socket 21 is hexalobe configured to receive a hexalobe configured bone screw installation tool (not shown).

Figure 7:
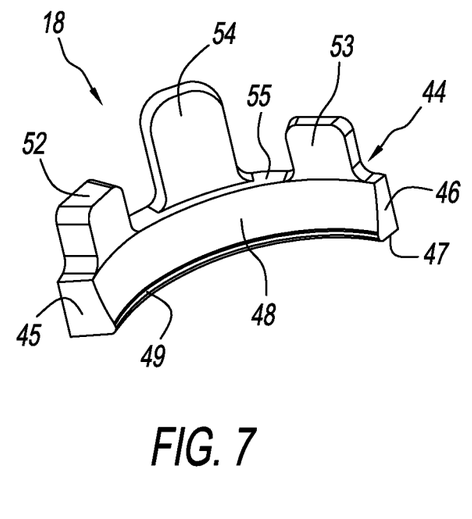
FIG. 7 is an enlarged perspective view of a closure of the modular pedicle screw of FIG. 1 showing one side thereof.
Figure 8:
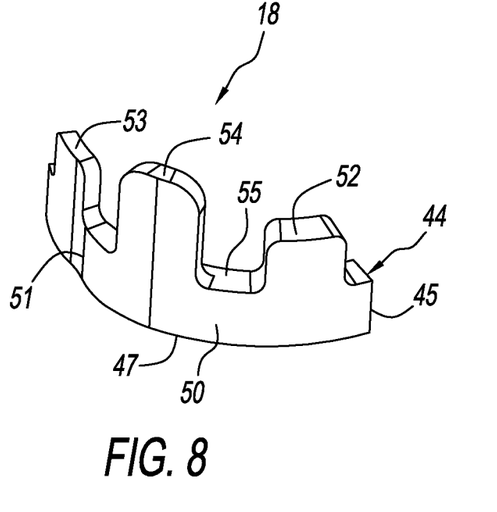
FIG. 8 is an enlarged perspective view of the closure of FIG. 7 showing an opposite side thereof.
Figure 13:
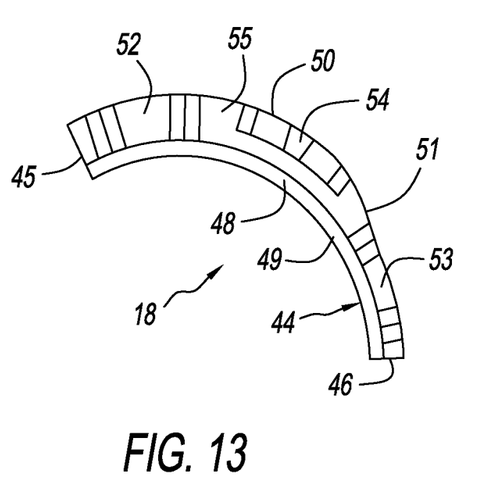
FIG. 13 is an enlarged top plan (axial) view of the closure of FIGS. 7 and 8.
Figure 14:
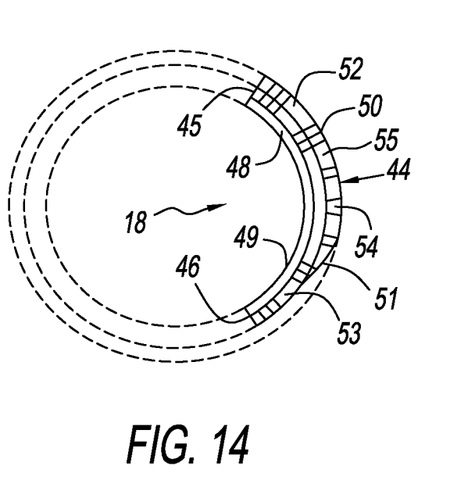
FIG. 14 is a top plan (axial) view of the closure of FIGS. 7 and 8 with three superimposed circles drawn thereon to highlight three characteristics of the closure.

Referring to FIGS. 7-8 and 13-14, a closure 18 is particularly shown. FIGS. 7-8 depict perspective views of the front and back sides of the closure 18, while FIGS. 13-14 depict axial plan views of the closure. The present pedicle screw assembly 10 can use from one (1) to three (3) closures 18, each one of them being the same as the other. The closure 18 is characterized by a generally curved body 44 having a bottom rim 49 and a generally flat top 55, the bottom 49 and top 55 axially separated from each other. A first flange 52 extends axially upward from the top 55 at one lateral side of the body 44. A second flange 53 extends axially upward from the top 55 at another lateral side of the body 44 opposite the one lateral side. The first and second lateral flanges 52, 53 each extend the depth of the top 55 such that the depth of the flange 52 is greater than the depth of the flange 53 due to the change in body thickness due to the interruption 51 and narrowing of the outer surface 50 of the body 44. The flanges 52 and 53 have generally the same width and height. A third flange 54 is disposed between the first and second flanges 52, 53 and extends axially upward from the top 55 higher than the first and second flanges 52, 53. The third flange 53 also has a greater width than the first and second flanges 52, 52. However, while the first and second flanges 52, 53 are generally flush with the inner surface 48 and the outer surface 50, the third flange is flush with only the outer surface 50 is radially inset from the inner surface 48.

The curved body 44 has an inner face or surface 48 that is curved radially inward to form a concave face between the bottom 49 and the top 55, and an outer face or surface 50 that is curved radially outward to form a convex face between the bottom 49 and the top 55. The body 44 has a first thickness 45 that extends radially along the body to an inflection, interruption, or variation area 51 where the thickness gradually decreases to a second thickness 46. Particularly, the outer surface 50 gradually decreases at the variation area 51. FIG. 14 depicts a top axial view of the closure 18 with three (3) dashed concentric circles superimposed thereon in order to highlight three (3) primary features of the closure 18. The largest (radially outermost) dashed circle corresponds to the outer surface 50 of the closure 18 which illustrates the interruption, inflection, or variation in the outer surface 50 of a radially inward curvature, causing a reduced body thickness and a camming or wedging surface that interacts with the interior chamber surface 37 of the head 26.

As indicated above, one or more closures 18 are used in the present pedicle screw assembly 10 and provide release and capture of the spherical proximal end 30 of the shank 14 in the head 12. A radial series of closures 18 create an opening that can be varied in diameter to contract and expand about the spherical proximal end 30 in order to capture and release the spherical proximal end 30 from the head 12. The closures 18 are received in the interior chamber 56 of the head 12. Rotation of the series of closures 18 in the internal chamber 37 provide an open state and a closed state through interaction between the geometry of the outside face 50 of the closure 18 and the internal chamber 56 of the head 12.

Figure 6:
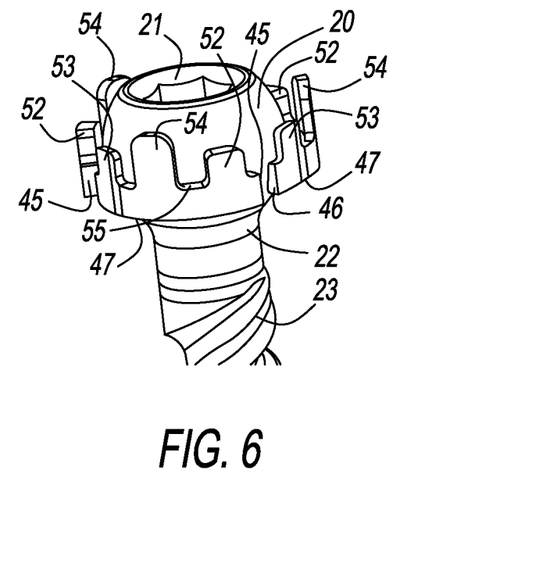
FIG. 6 is an enlarged perspective view of three closures around the spherical proximal end of the shank of the modular pedicle screw of FIG. 1.
Figure 9:
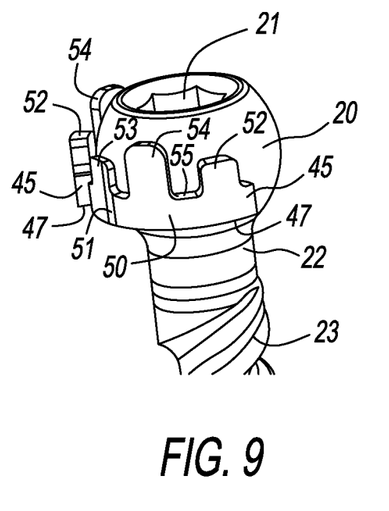
FIG. 9 is an enlarged perspective view of two closures around the spherical proximal end of the shank of the modular pedicle screw of FIG. 1.
Figure 10:
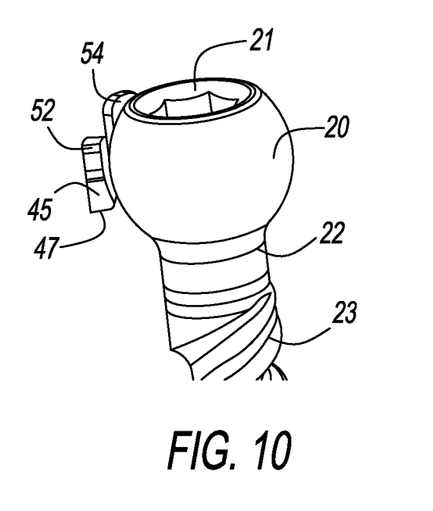
FIG. 10 is an enlarged perspective view of one closure around the spherical proximal end of the shank of the modular pedicle screw.

FIG. 10 illustrates how one (1) closure extends around the proximal spherical head 20 of the shank 14. FIG. 9 illustrates how two (2) closures extend around the proximal spherical head 20 of the shank 14. FIG. 6 illustrates how three (3) closures extend around the proximal spherical head 20 of the shank 14.

Figure 19:
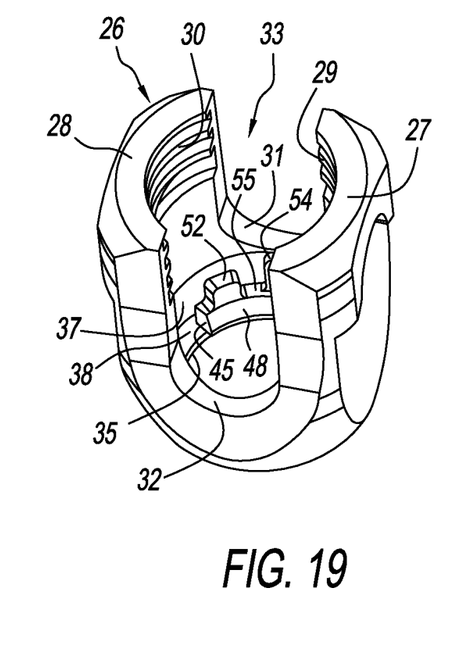
FIG. 19 is an enlarged isometric view of the head of the modular pedicle screw of FIG. 1 with one closure in the chamber of the lower portion of the head of the modular pedicle screw of FIG. 1.
Figure 20:
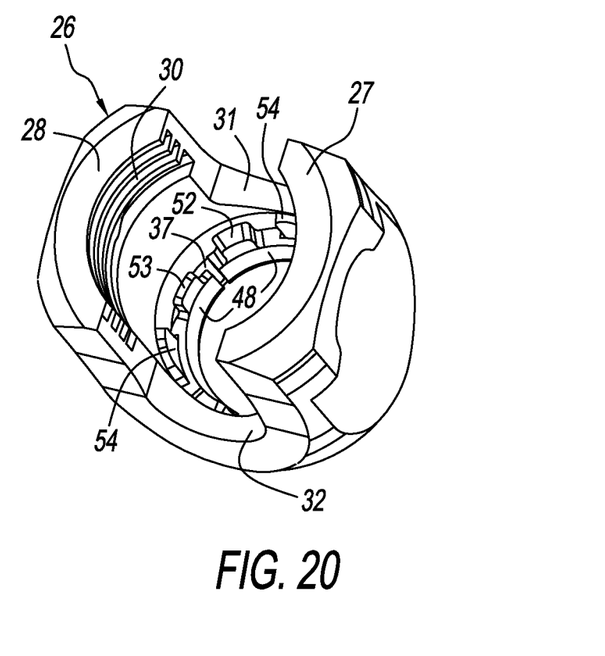
FIG. 20 is an enlarged isometric view of the head of the modular pedicle screw of FIG. 1 with two closures in the chamber of the lower portion of the head of the modular pedicle screw of FIG. 1.
Figure 21:
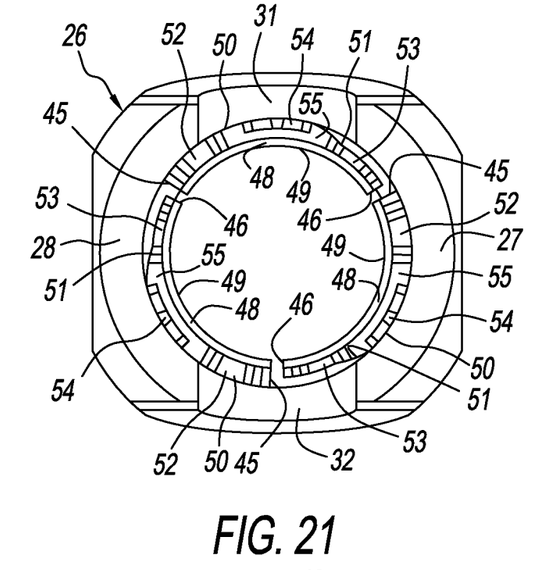
FIG. 21 is a top plan (axial) view of the chamber of the lower portion of the head of the modular pedicle screw of FIG. 1 with three closures in a closed state.
Figure 22:
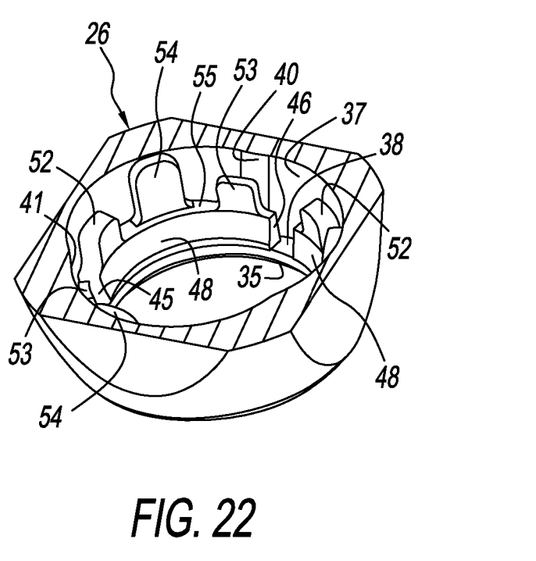
FIG. 22 is an enlarged sectional isometric view of the chamber of the lower portion of the head of the modular pedicle screw of FIG. 1 with three closures in an open state.
Figure 23:
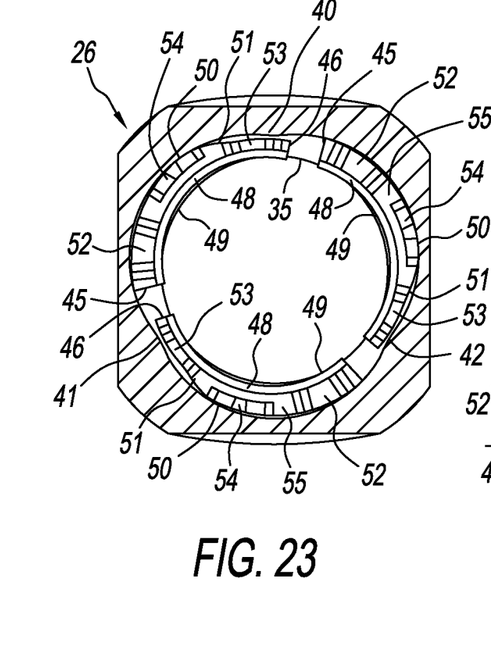
FIG. 23 is a top plan (axial) sectional view of the chamber of the lower portion of the head of the modular pedicle screw of FIG. 1 with three closures in the open state.
Figure 24:
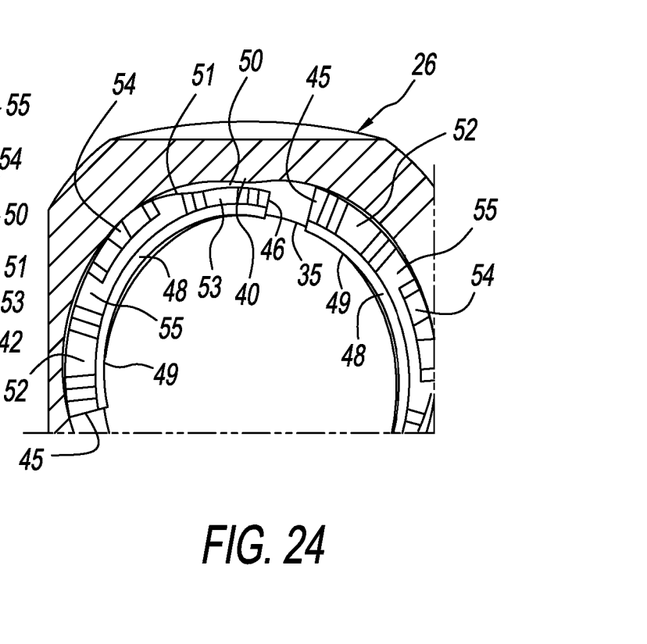
FIG. 24 is an enlarged close-up top plan (axial) sectional view of a portion of the chamber of the lower portion of the head of the modular pedicle screw of FIG. 1 showing two of three closures in the open state, allowing for the largest possible through passage wherein a shank can be introduced therein.
Figure 25:
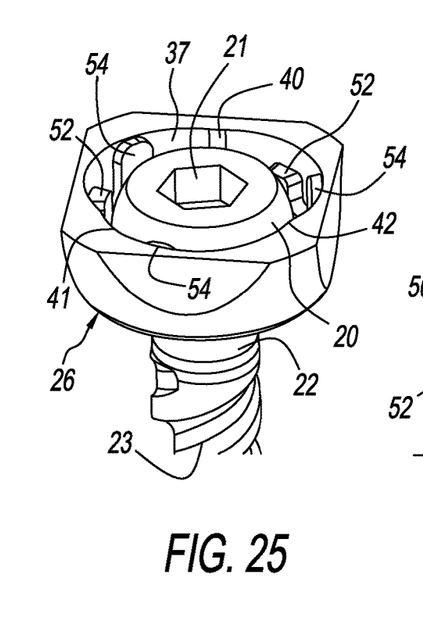
FIG. 25 is an enlarged sectional isometric view of the chamber of the lower portion of the head of the modular pedicle screw of FIG. 1 with three closures in the open state with the spherical proximal end of the shank introduced therein.
Figure 26:
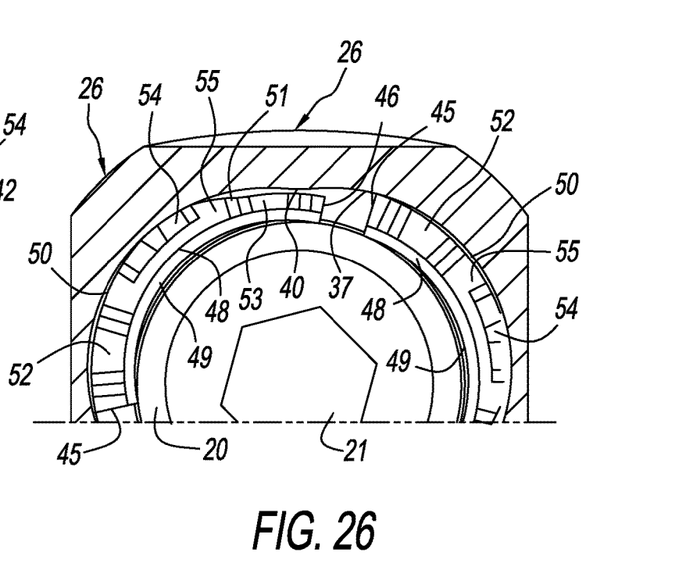
FIG. 26 is an enlarged top plan (axial) sectional partial view of the chamber of the lower portion of the head of the modular pedicle screw of FIG. 1 showing two of three closures in the chamber in the open state with the spherical proximal end of the shank introduced therein.

The manner of interaction of the closures 18, the spherical proximal head 20 of the shank 14, and the internal chamber 56 of the head 12 are illustrated in FIGS. 19-33. FIG. 19 shows a single (1) closure 18 situated in the interior chamber 56 of the head 12. FIG. 20 shows two (2) closures 18 situated in the interior chamber 56 of the head 12. FIG. 21 shows three (3) closures 18 situated in the internal chamber 56 of the head 12, the closures in an open state. As indicated, two (2) states are possible with the head and closures subassembly, an open state that allows the passage of the proximal spherical end 20 of the shank 14, and a close state that captures the proximal spherical end 20 of the shank 14 and prevent it from disassembly from the head 12. The state of change is created from positional rotation of the closures 18 about a central axis of and relative the head 12 within the interior chamber 56. In order to allow introduction of the shank 14, the through hole created by the inner edge 49 of the closures 18 is such that it is close to or slightly larger than the diameter of the proximal spherical end 20 of the shank 14. This is possible when the outer most surfaces of the closures 18 are in a first angular (rotational) position within the interior chamber 56 such that the thin ends 46 thereof are adjacent or proximate and the thick end 45 is not on, the interruptions 40, 41, 42 of the surface 37 of the interior chamber 56. FIGS. 22-24 show three (3) closures in the interior chamber 56 of the head 12 in the open state by their angular/rotational position in the interior chamber 56 such that they create the largest through diameter possible. FIGS. 25-26 shows the same as FIGS. 22-24 but with the introduction of the proximal spherical end 20 therein.

Figure 27:
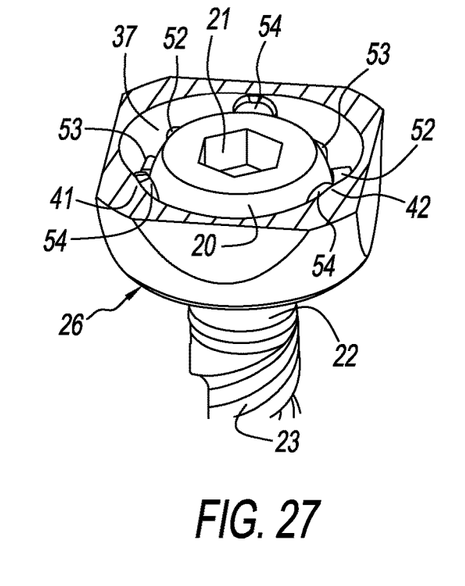
FIG. 27 is an enlarged sectional isometric view of the chamber of the lower portion of the head of the modular pedicle screw of FIG. 1 with three closures in the closed state with the spherical proximal end of the shank captured therein.
Figure 28:
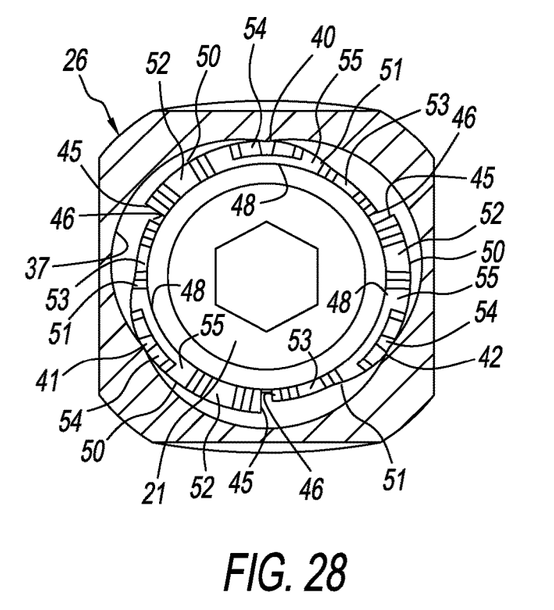
FIG. 28 is an enlarged top plan (axial) sectional view of the chamber of the lower portion of the head of the modular pedicle screw of FIG. 1 with three closures in the closed state with the spherical proximal end of the shank captured therein.
Figure 29:
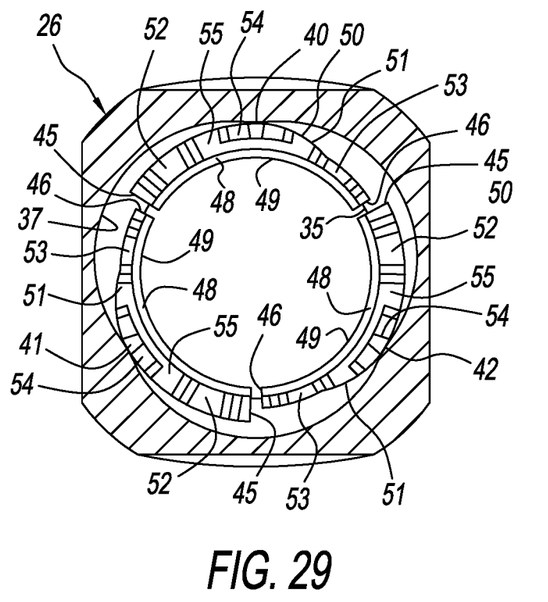
FIG. 29 is an enlarged top plan (axial) sectional view of the chamber of the lower portion of the head of the modular pedicle screw of FIG. 1 with three closures in the closed state.
Figure 30:
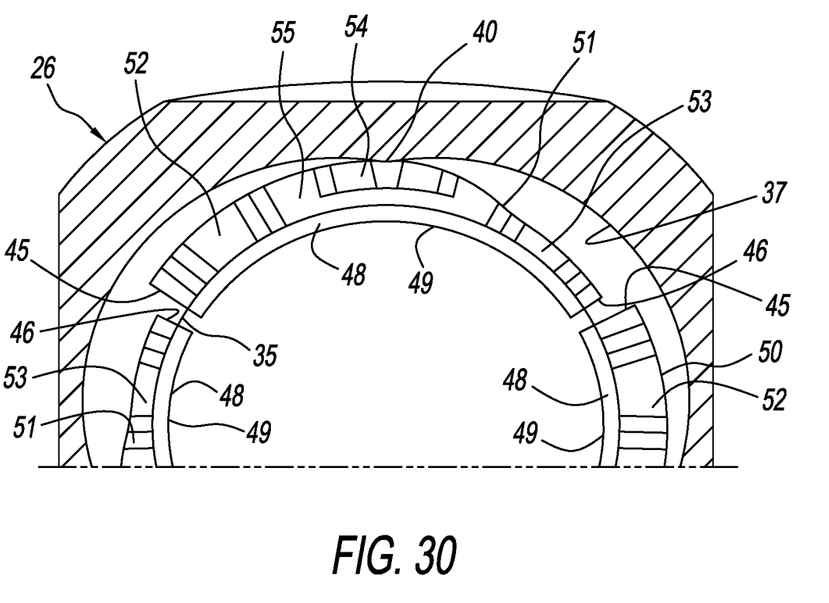
FIG. 30 is an enlarged close-up top plan (axial) sectional view of a portion of the chamber of the lower portion of the head of the modular pedicle screw of FIG. 1 showing two of three closures in the closed state not allowing for the passage or introduction of the shank therein shown without the shank.
Figure 31:
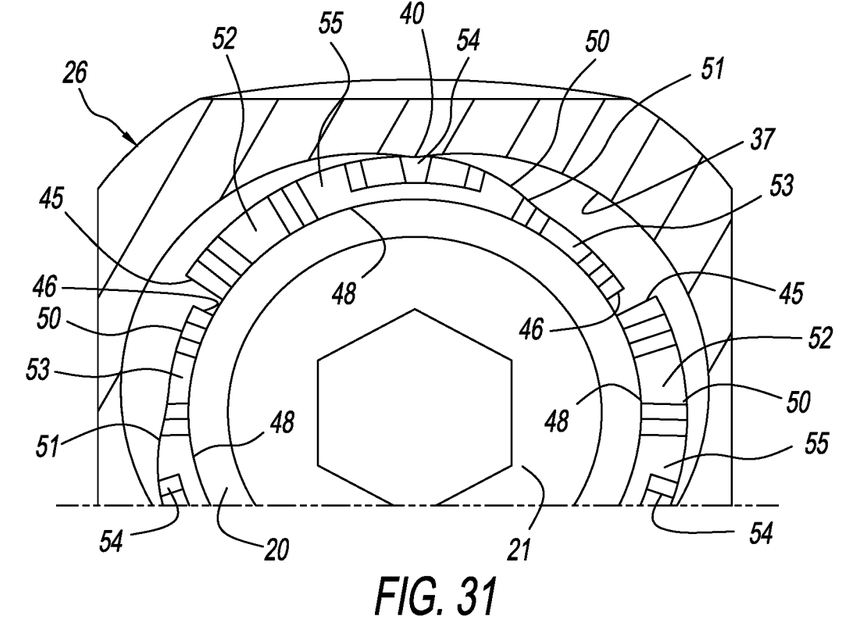
FIG. 31 is an enlarged close-up top plan (axial) sectional view of a portion of the chamber of the lower portion of the head of the modular pedicle screw of FIG. 1 showing two of three closures in the closed state, with the spherical proximal end of the shank captured therein.

FIGS. 27-31 show various views of the closed state wherein the shank is captured and prevents the assembly from disassembly. The closed state is achieved by rotating the closures 18 about the central axis of the head 12 to a second position. This second position puts the outer most surface 50 of the closures 18 adjacent the inner most surfaces (i.e. the interruptions 40, 41, 42) of the internal chamber 56 in the head 12. This effectively reduces the through diameter to a value that will not permit the proximal spherical end 20 of the shank 14 to pass back through. The transition from an open state to a closed state involves the geometric interruption on the inside of the chamber to cam or wedge against the geometric interruption on the outside of the closures, forcing a radial translation of the closures, narrowing the through passage of the subassembly. FIGS. 27, 28 and 31 show the spherical proximal end 20 captured. FIGS. 29 and 30 show the closed state but without the shank 14.

Figure 32:
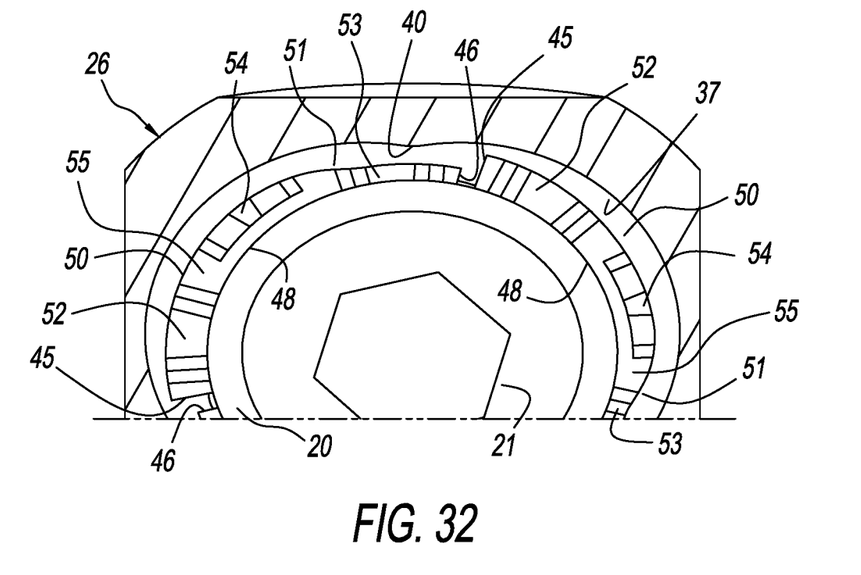
FIG. 32 is an enlarged close-up top plan (axial) sectional view of a portion of the chamber of the lower portion of the head of the modular pedicle screw of FIG. 1 showing two of three closures rotated into the open state, showing the spherical proximal end of the shank.
Figure 33:
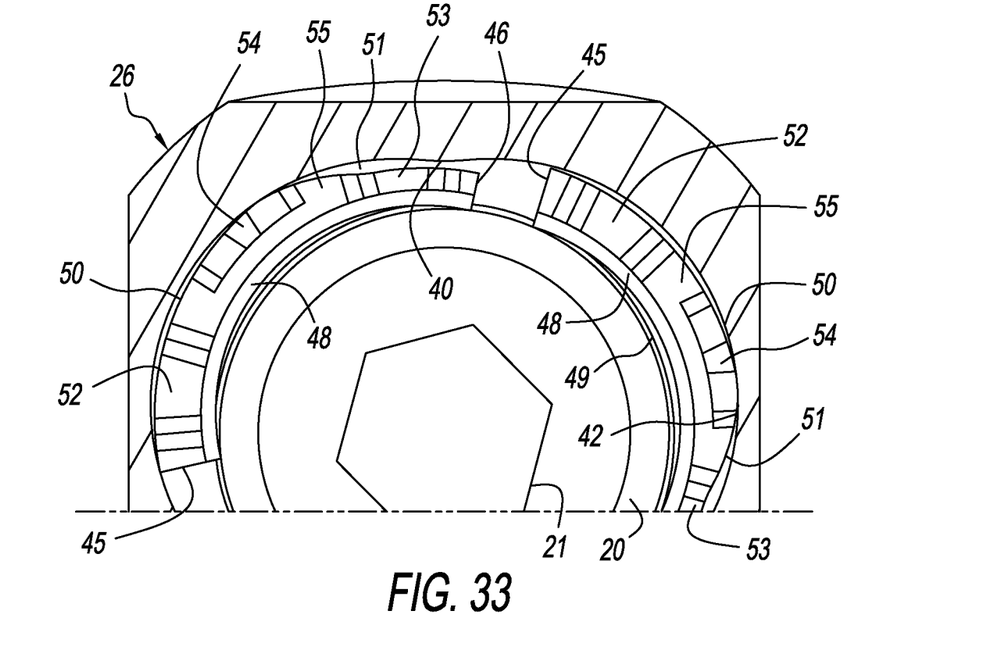
FIG. 33 is an enlarged close-up top plan (axial) sectional view of a portion of the chamber of the lower portion of the head of the modular pedicle screw of FIG. 1 showing two of three closures rotated into the open state, showing the spherical proximal end of the shank being pulled through, forcing the closures outward.
Figure 34:
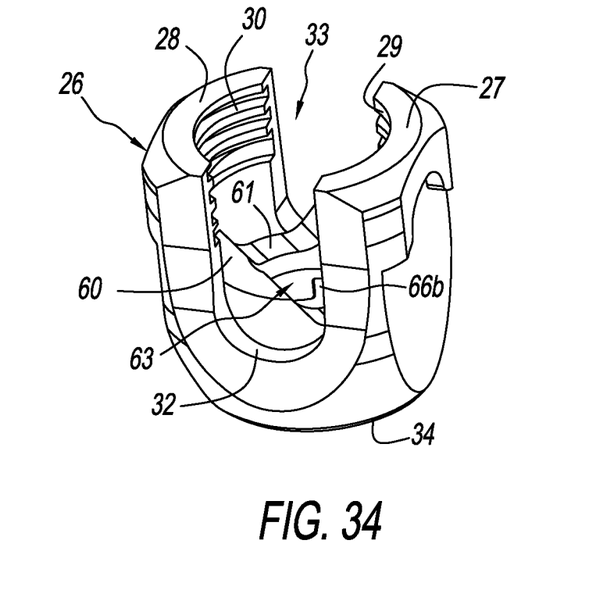
FIG. 34 is an enlarged isometric view of the head, closures, and ring assembly in an open state.

The transition from the open state to the closed state is reversible. An equal rotation of the closures 18 in the opposite rotational direction back to the open state will create space for the closures 18 to translate radially back into, effectively opening back up the through diameter of the subassembly so that the shank 14 may be disengaged. Once the open state has been regained, a force is introduced to pull the subassembly off of the shank. This will force the closures 18 radially outward to restore the large through diameter. FIG. 32 shows the closures 18 rotated back into an open state with the proximal spherical end 20 still present. FIG. 33 shows the closures 18 rotated back into an open state with the proximal spherical end 20 pulled therethrough.

Figure 5:
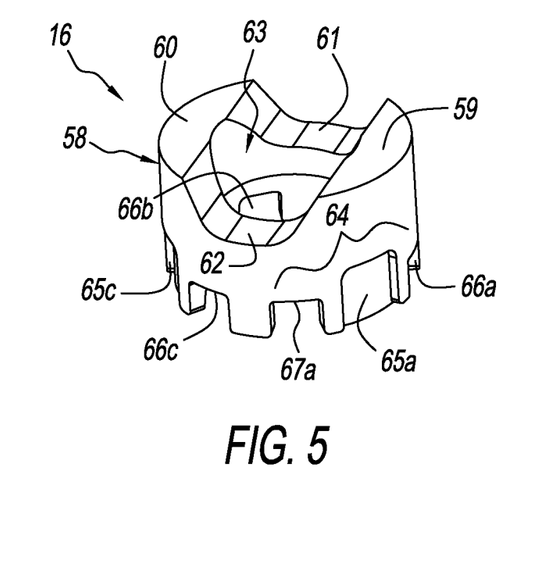
FIG. 5 is an enlarged perspective view of the ring of the modular pedicle screw of FIG. 1.
Figure 12:
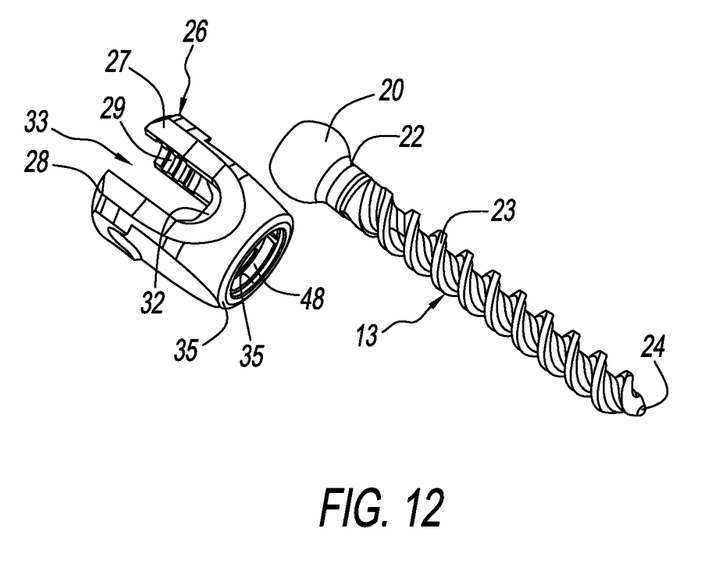
FIG. 12 is a perspective view of the bone screw and head of the modular pedicle screw of FIG. 1.
Figure 36:
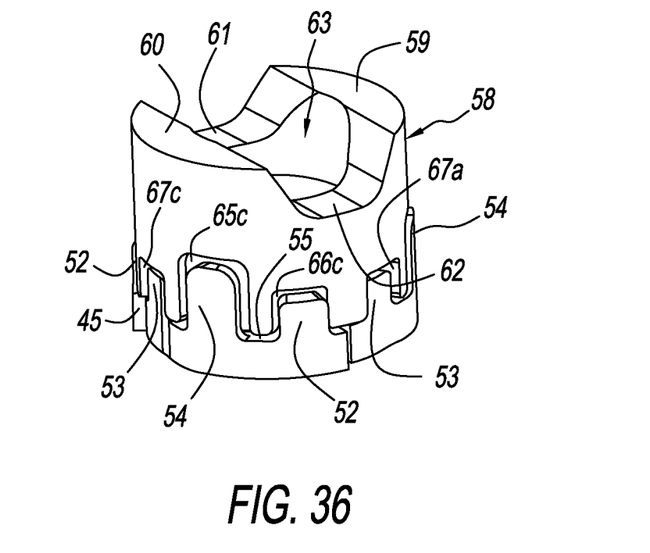
FIG. 36 is an enlarged isometric view of the ring and closures therein illustrating the interdigitated flanges of the ring and closures for torque transmission between the ring and the closures.

The ring 16 is shown in FIG. 5. The ring 16 is defined by a generally cylindrical body 58 with a first cutout 61 in one axial end and a second cutout 62 in the same axial end as the first cutout 61 but disposed radially opposite thereto. The first and second cutouts 61, 62 shaped to receive a cylindrical spine rod (not shown) therein. The first and second cutouts 61, 61 forming a first side wall 59, and a second side wall 60 radially opposite the first side wall 59. These formations creating a saddle shape. An axial bore 63 is provided in the body 58 extending through the body 58 from the axial top to the axial bottom thereof. A plurality of central notches 65*a-c* are cut into the bottom circumference of the body 58. Each central notch 65*a-c* is configured to receive the third flange 54 of a closure 18 and thus do not extend entirely through the body 58 since the third flange 54 is offset on the top 55 of the closure 18. The central notches 65*a-c* are spaced about the circumference of the body 58 accordingly. A plurality of first lateral notches 66*a-c* are provided in the bottom circumference of the body 58 that extend entirely therethrough. Each first lateral notch 66*a-c* is configured to receive the first lateral flange 52 of a closure 18. The first lateral notches 66*a-c* are spaced about the circumference of the body 58 accordingly. A plurality of second lateral notches 67*a-c* are provided in the bottom circumference of the body 58 that extend entirely therethrough. Each second lateral notch 67*a-c* is configured to receive the second lateral flange 53 of a closure 18. The second lateral notches 66*a-c* are spaced about the circumference of the body 58 accordingly. The inter-digitation of the ring 16 and the closures 18 is shown in FIG. 36. With the ring 16, the subassembly consisting of the head 12, ring 16 and closures 18 can receive the shank 14 as shown in FIG. 12.

Figure 3:
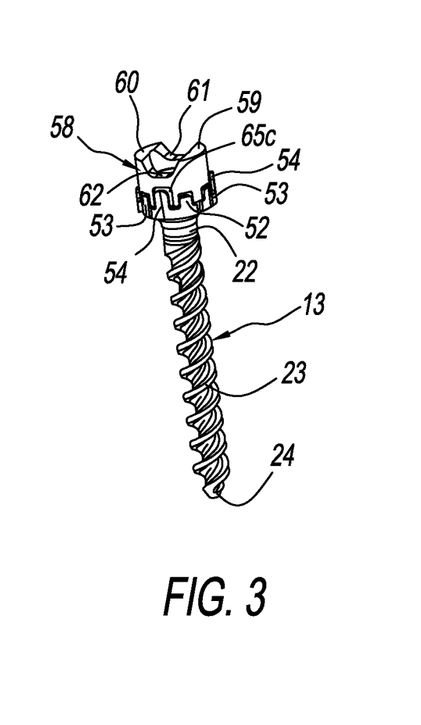
FIG. 3 is a perspective view of the modular pedicle screw of FIG. 1 with the head removed to show a ring and closures on a spherical proximal end of a shank of the modular pedicle screw of FIG. 1.
Figure 4:
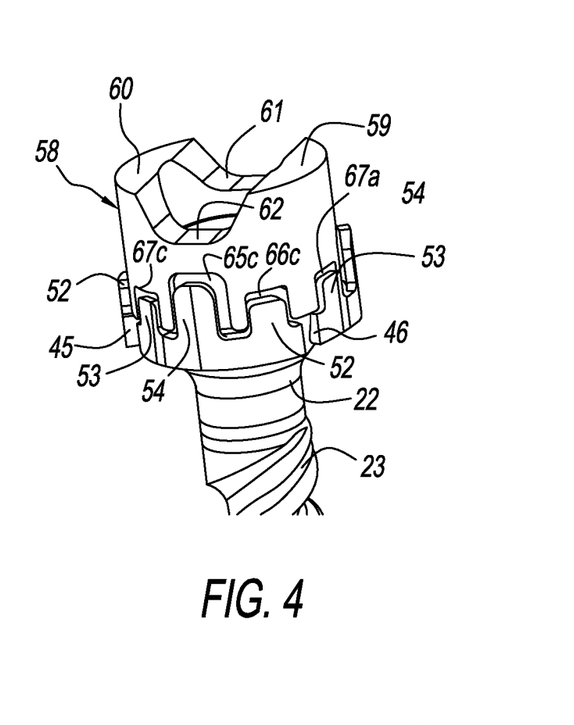
FIG. 4 is an enlarged perspective view of the ring and closures on the spherical proximal end of the shank of the modular pedicle screw of FIG. 1.

In addition to the ring 16 being received or fit to the ring 16 in an inter-digitation manner, the ring 16 is configured to be received onto and over the spherical proximal end 20 of the shank 14 and fit onto the radial series of closures 18 such as seen in FIGS. 3 and 4. The ring 16 provides a manner of rotating the series of closures 18 to provide the open and closed states.

Figure 35:
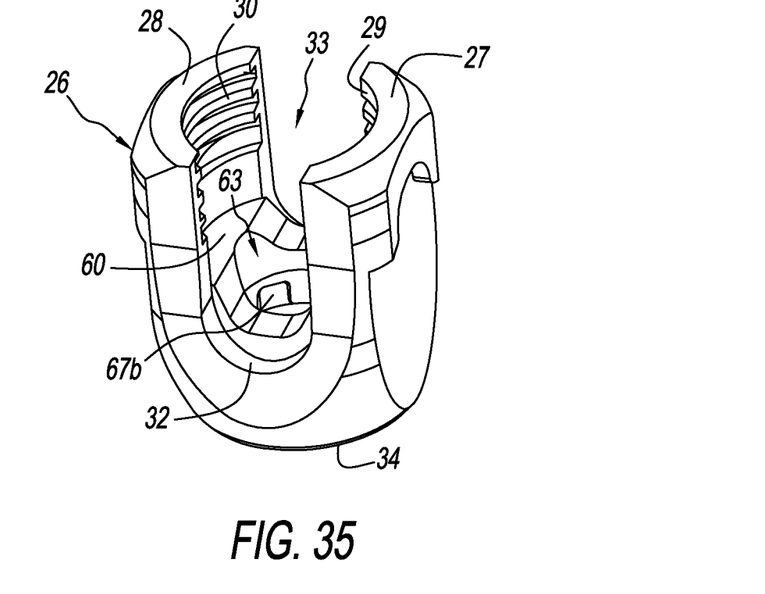
FIG. 35 is an enlarged isometric view of the head, closures, and ring assembly in a closed state.

Rotation of the closures 18 is created with an applied torque to the ring 16. As shown in FIG. 35, misalignment of the rod slot formed by the cutouts 61, 62 of the ring with the rod slot of the head created by cutouts 31, 32 indicates an open state. When the closed state has been reached, the rod slot of the ring 16 is parallel with that of the head 12 as shown in FIG. 35.

Torque is translated through the ring 16 into the closures 18 via a loose mechanical attachment. This attachment is preferably, but not necessarily, an inter-digitation of axial flanges of the closures and ring, and slots for the flanges of the closures in the ring. The flanges of the ring apply a tangential force to those of the closure.

While the invention has been illustrated and described in detail in the drawings and foregoing description, the same is to be considered as illustrative and not restrictive in character, it being understood that only a preferred embodiment has been shown and described and that all changes and modifications that come within the spirit of the invention are desired to be protected.

What is claimed is:

1. A pedicle screw for holding a spine rod in a fixed spatial orientation relative to a vertebra, the pedicle screw comprising:
    a shank having an externally threaded shaft defining a distal end and a proximal spherical end having a configured socket;
    a head having a top, a bottom, a bore extending from the top to the bottom and defining a circumferential wall, a central axis, a top opening, a bottom opening, and an interior with a radial wall, a chamber formed in the interior proximate the bottom opening, the chamber having a circumferential surface radially inset from the radial wall, the circumferential surface having a plurality of curved protrusions extending radially inward toward the central axis, each one of the plurality of curved protrusions circumferentially spaced from one another;
    a plurality of closures equal in number to the plurality of curved protrusions and disposed in radial series in the chamber of the head, each closure having a curved body with a top surface, a first end, a second end, an inside surface, an outside surface, a first flange extending from the top surface proximate the first end, a second flange extending from the top surface proximate the second end, a third flange extending from the top surface between the first flange and the second flange, a first width extending from the first end to proximate the second end, a second width extending from the second end to the first width proximate the second end, and a sloping surface extending between the first width and the second width, the plurality of closures situated in the chamber of the head, wherein rotation of the closures provides capture and release of the spherical end of the shank by the head through cam action between the closures and the internal chamber to increase and decrease size of an opening formed by the closures; and a cylindrical ring disposed in the bore of the head axially above the chamber, and having an outer circumference, a top, a bottom, and a plurality of notches in the bottom and spaced about the outer circumference and configure to receive first, second, and third flanges of the plurality of closures in radial series in the chamber, whereby rotation of the ring rotates the plurality of closures in radial series in the chamber to provide capture and release of the spherical head of the shank by the plurality of closures.

2. The pedicle screw assembly of claim 1, wherein the first flange of each closure of the plurality of closures has a first height, the second flange of each closure of the plurality of closures has a second height that is equal to the first height, and the third flange of the each closure of the plurality of closures has a third height that is taller than the first and second heights.

3. The pedicle screw assembly of claim 2, wherein the first flange of each closure of the plurality of closures has a first depth that extends from the inside surface to the outside surface, the second flange of each closure of the plurality of closures has a second depth that extends from the inside surface to the outside surface, and the third flange that has a third depth that extends from the outside surface to a middle of the top surface that is between the outside surface and the inside surface.

4. The pedicle screw assembly of claim 3, wherein:
the circumferential wall of the head has a first trough extending from the top of the head to proximate the chamber of the head, and a second trough extending from the top of the head to proximate the chamber of the head, the first and second troughs defining a spine rod holder; and
the cylindrical ring has a first depression in the top, and a second depression in the top, the first and second depressions defining a second spine rod holder;
wherein when the second spine rod holder of the cylindrical ring misalign with the spine rod holder of the head, the closures are in an open state, and when the second spine rod holder of the cylindrical ring aligns with the spine rod holder of the head, the closures are in a closed state.

5. The pedicle screw assembly of claim 1, wherein the interior chamber has a bottom ledge that receives each bottom of the plurality of closures.

6. The pedicle screw assembly of claim 1, wherein:
the circumferential surface of the chamber has an upper end defined by a radially inward undercut and a bottom ledge; and
each one of the curved protrusions axially extends from upper end to the bottom ledge.

* * * * *